United States Patent [19]

Lowell

[11] 4,306,547
[45] Dec. 22, 1981

[54] RIGID FIBEROPTIC LARYNGOSCOPE

[76] Inventor: James R. Lowell, 3721 Fry, Tyler, Tex. 75701

[21] Appl. No.: 95,950

[22] Filed: Nov. 20, 1979

[51] Int. Cl.³ .............................................. A61B 1/26
[52] U.S. Cl. ...................................... 128/11; 128/16; 128/200.26
[58] Field of Search .................... 128/4, 6, 11, 16, 13, 128/200.26

[56] References Cited

U.S. PATENT DOCUMENTS

| 3,426,749 | 2/1969 | Jephcott | 128/11 |
| 3,592,199 | 7/1971 | Ostensen | 128/6 |
| 3,595,222 | 7/1971 | Vellacott | 128/11 |
| 3,598,113 | 8/1971 | Moore | 128/11 |
| 3,616,792 | 11/1971 | Pleet | 128/11 |
| 3,638,644 | 2/1972 | Reick | 128/16 |
| 3,766,909 | 10/1973 | Ozbey | 128/11 |
| 3,856,001 | 12/1974 | Phillips | 128/16 X |
| 3,913,568 | 10/1975 | Carpenter | 128/11 |
| 3,986,854 | 10/1976 | Scrivo | 65/4 R |

Primary Examiner—Michael H. Thaler
Attorney, Agent, or Firm—Shlesinger, Arkwright, Garvey & Dinsmore

[57] ABSTRACT

A rigid laryngoscope having a forwardly extending blade and an instrument supporting channel. The laryngoscope includes a viewing assembly and light source each connected to fiber optic bundles.

2 Claims, 7 Drawing Figures

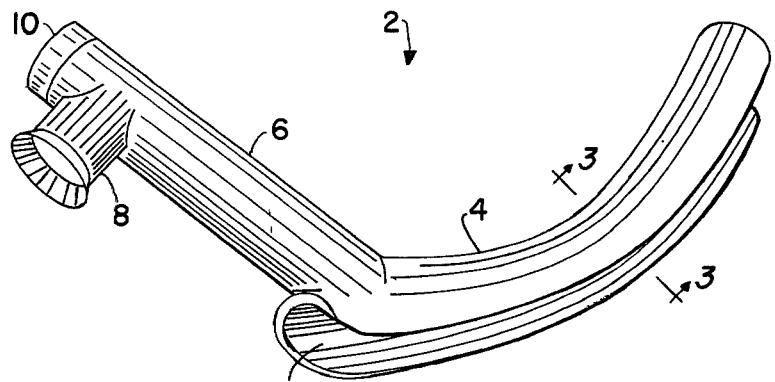
Fig 1
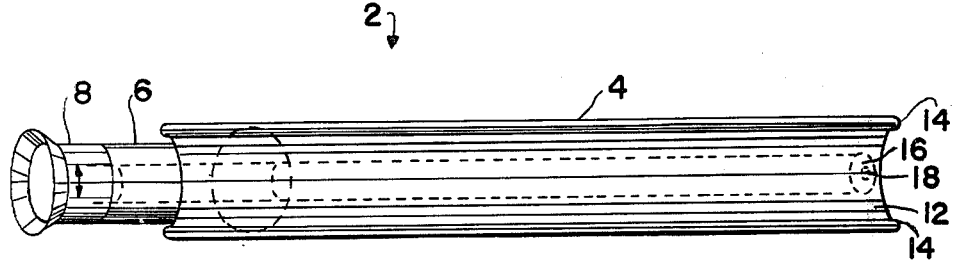
Fig 2
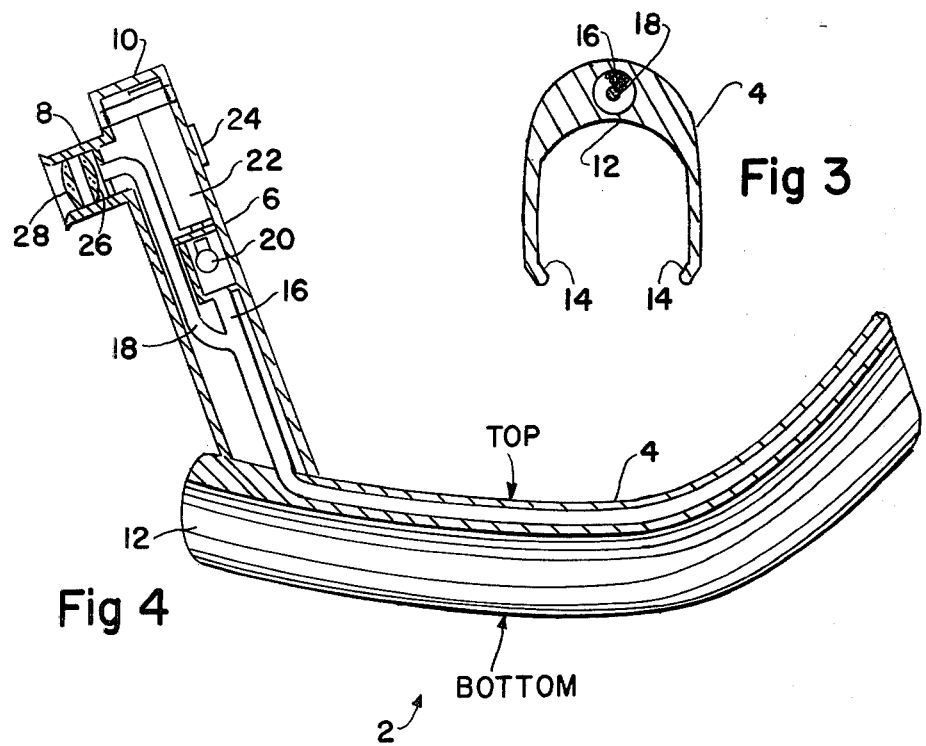
Fig 3
Fig 4

RIGID FIBEROPTIC LARYNGOSCOPE

BACKGROUND OF THE INVENTION

This invention relates to medical instruments. In particular, it relates to a laryngoscope for use in diagnosis, biopsy, the introduction of instruments or tubes into the trachea, and other like operations.

In the past, laryngoscopy was performed using laryngoscopes with either curved or straight blades. The choice of blade shape depended on which of two methods the physician preferred. The two methods are, however, only slightly different. In either method, the purpose of the blade is to push the tongue and other soft structures of the upper anterior neck forward. This displacement would permit a straight line of vision from the patient's upper teeth to the larynx. However, in some cases the head of the patient could not be adequately extended; this would prohibit the physician from seeing the larynx. Additionally, with either the straight or curved blade, intensive pressure was required to move the anatomic structures. In exerting the required pressure, the physician would sometimes have to pry against the patient's upper teeth. This, of course, introduced the possibility of damage to the patient's teeth.

Once a line-of-sight was obtained between the patient's upper teeth and the larynx, the physician was still faced with the problem of getting enough light to illuminate the larynx in order to see the larynx. Laryngoscopes which had illuminating provisions were of generally two types. The first type incorporated a light bulb at the tip of the laryngoscope. Typical of these is the patent to Vellacotie U.S. Pat. No. 3,595,222. This light bulb would give off considerable heat. As such, there was the possibility of burning the larynx of the patient. Also, in certain operations, blood might be present around the tip of the laryngoscope where the light bulb was housed. In this case, the heat from the light bulb tended to encrust the blood around the light bulb. This severely reduced the illumination of the larynx.

The second type of illuminating laryngoscope incorporated a light ducting means to guide the light from the light bulb to the tip of the blade. The light bulb was typically mounted within the handle of the laryngoscope. With the light bulb mounted in the handle the heat problem was eliminated. However, this posed the problem of getting enough light from the light bulb to the tip of the blade in order to illuminate the larynx. Some laryngoscopes incorporated lucite or plexiglass light guides. Typical of these is the patent to Reich, U.S. Pat. No. 3,638,644. Lucite and plexiglass light guides emit light around the entire circumference of the guide. Additionally "lucite" and "plexiglass" have a high coefficient of attenuation to light. This reduces the amount of light available at the tip of the laryngoscope. Also, acrylic resins such as "lucite" are lacking in the required mechanical properties. Lucite is a very brittle material and tends to crack with age. A crack in lucite is a glassy fracture. This fracture can reflect as much light back to the source as passes through the fracture. An additional problem with lucite is that is cannot be sterilized by boiling water. In order to sterilize and at the same time prevent the lucite from softening, chemicals such as ethylene oxide must be used.

OBJECT OF THE INVENTION

In view of the foregoing, an object of the present invention is to provide a laryngoscope which reduces the amount of pressure used against the tongue and other soft structures of the upper anterior neck during laryngoscopy.

Still another object of the invention is to provide a laryngoscope which safely illuminates the larynx.

A further object of the invention is to provide a laryngoscope which incorporates a light guide and lens assembly to enable visual examination of the larynx.

An additional object of the invention is to provide a self-contained illumination source.

Still a further object of the invention is to provide light guides for both illumination and vision which do not crack with age.

Another object of the invention is to provide a laryngoscope with an operating channel which permits removal of the laryngoscope without retracting tools or tubes from the larynx of the patient, which were inserted by the laryngoscope.

Still another object of the invention is to provide a laryngoscope which does not damage the patient's teeth when in use.

These and other objects of this invention will be apparent in the accompanying specification and drawings which illustrate by way of example an embodiment of this invention.

DESCRIPTION OF THE DRAWINGS

FIG. 1 is a side elevational view of the laryngoscope.

FIG. 2 is a top view showing in phantom lines the fiber optic channel.

FIG. 3 is a cross sectional view of the laryngoscope blade taken along lines 3—3 of FIG. 1.

FIG. 4 is a cut away side elevational view showing the viewing lens assembly, the light bulb, battery and switch, and the fiber optic bundles.

FIGS. 1 THROUGH 4

Figure 5:
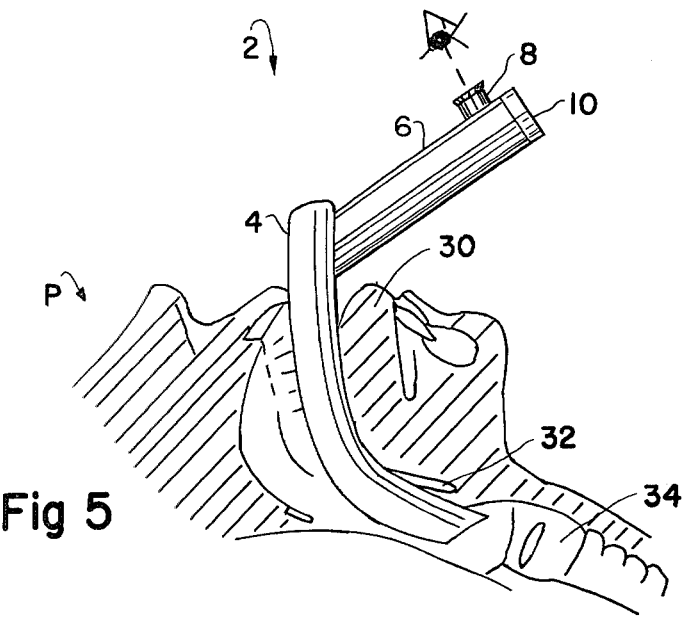
FIG. 5 is an operational view showing the laryngoscope in position within the mouth of the patient.

The laryngoscope 2 has a blade 4 and a handle 6. The handle 6 has protruding from it the viewing assembly 8. End cap 10 screws on to the bottom of handle 6. Integral to the blade 4 is an operating channel 12. The blade 4 also has retaining edges 14.

Within the blade 4 and handle 6 are two fiber optic bundles 16 and 18. Fiber optic bundle 16 is in operational alignment with light bulb 20 which is in turn connected to both the battery 22 and the switch 24. The two lenses 26 and 28 are in operational alignment with the end of fiber optic bundle 18.

Figure 6:
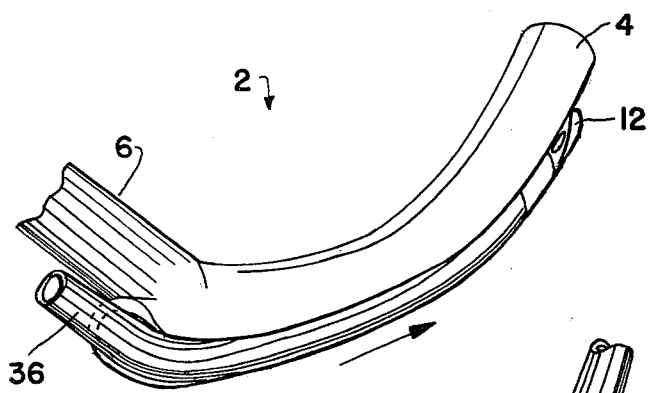
FIG. 6 is a partial side elevational view of the laryngoscope showing a tube in the operating channel.
Figure 7:
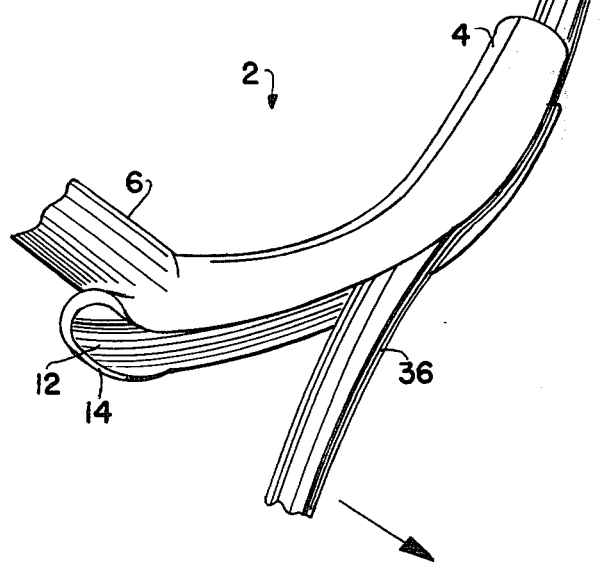
FIG. 7 is a partial side elevation view of the laryngoscope showing a tube half way out of the operating channel.

FIGS. 5, 6, and 7

Referring now to FIG. 5, the laryngoscope blade 4 is positioned around the circumference of the tongue 30 and epiglottis 32 of patient P. The tip of the blade 4 is positioned axially with respect to the larynx 34.

FIGS. 6 and 7

The operating channel 12 has retained in it a tube 36. In FIG. 6 the tube 36 is retained along the entire length of the operational channel 12 while in FIG. 7 the tube 36 is half way extracted from the operating channel 12.

OPERATION OF THE INVENTION

The laryngoscope 2 has a circulinear blade 4 which is integral with the top of the handle 6. Lens assembly 8 is located close to the end cap 10. End cap 10 can be unscrewed to provide access to the interior of handle 6.

Operating channel 12 is constructed in a "U" shape and has retaining edges 14. The retaining edges 14 serve to keep tubes or other instruments secured within the operating channel 12. As is best shown in FIG. 3, fiber optic bundles 16 and 18 are in coaxial alignment with bundle 18 in the center.

Referring now to FIG. 4, fiber optic bundle 16 is in axial alignment with the light bulb 20. This permits the light from bulb 20 to be ducted to the other end of bundle 16 at the tip of blade 4. The battery 22 is connected to light bulb 20 through switch 24. This permits the light bulb 20 to be switched on and off.

Fiber optic bundle 18 is in axial alignment with lenses 26 and 28, within viewing assembly 8. The two lenses 26 and 28 serve to focus the light emitted from the end of bundle 18 into a visual image. By turning the viewing assembly 8 the focus can be changed.

Referring now to FIG. 5, the laryngoscope 2 is in the operating position within patient P. The blade 4 curves around the posterior of the tongue 30 and epiglottis 32. Since the blade curves around these structures 30 and 32, excessive force is not exerted on them. As is shown in FIG. 5, a line-of-site from the patients teeth to the larynx 34 is not required. By looking into the viewing assembly 8 the image of the larynx 34, ducted by the fiber bundle 18, can be seen.

If intubation is required, a tube can be secured within the operating channel 12 (FIG. 6). This tube 36 can be directed into the larynx 34 by inserting the laryngoscope 2 in the operating position within the patient P. Once the tube 36 is in place within the patient P, the laryngoscope 2 can be removed by forcing tube 36 out of the operating channel 12 (FIG. 7).

As is now readily understood from the above, because the blade 4 curves around the tongue 30 and epiglottis 32, extensive force is not required to use the laryngoscope 2. As such, the chance of damage to the patients P teeth is greatly reduced if not eliminated. Additionally, since the ends of the fiber optic bundles 16 and 18 are substantially flush with the tip of blade 4, the chance of damage to either of the fiber optic bundles 16 or 18 is minimal.

While this invention has been described as having a preferred design, it will be understood that it is capable of further modification. This application is, therefore, intended to cover any variations, uses, or adaptations of the invention following the general principles thereof and including such departures from the present disclosure as come within known or customary practice in the art to which this invention pertains, and as may be applied to the essential features hereinbefore set forth and fall within the scope of this invention or the limits of the claims.

What is claimed is:

1. A laryngoscope having:
   (a) a handle having a side, top and bottom and including a light source and a lens assembly
   (b) a curvilinear blade having front and rear ends and a top and bottom
   (c) said blade being U-shaped in cross section from said front to said rear ends and forming a channel having bottom and side walls and having the legs of said U extending away from said handle substantially equal distances from said bottom wall
   (d) said channel bottom wall having an inside and outside surface and a front end face
   (e) said channel bottom wall being substantially thicker than said channel side walls
   (f) an opening in said front face
   (g) said handle being positioned inside the curve of said blade and being connected to said outside surface of said channel bottom wall at said rear end of said blade
   (h) said channel opening in a direction away from said handle connection
   (i) a first optical light transmitting means aligned with said light source
   (j) a second optical light transmitting means aligned with said lens assembly
   (k) said first and second light transmitting means extending from said handle into said blade and to said front end of said blade and ending in said opening in said channel bottom wall front end face for projecting light from said face which is received from said light source and receiving reflected light onto said face for directing it to said lens assembly
   (l) said first and second optical light transmitting means being positioned interior of and spaced from said inside and outside surfaces of said channel bottom wall, and said channel side walls having side wall edge flanges angled inwardly from said channel side walls for maintaining an attachment in said channel, and
   (m) said side wall edge flanges extending substantially the entire length of said channel.

2. A laryngoscope as in claim 1 and wherein:
   (a) said lens assembly is mounted on the side of said handle.

* * * * *